United States Patent [19]

Lauer et al.

[11] Patent Number: 5,447,611

[45] Date of Patent: * Sep. 5, 1995

[54] VACUUM INJECTION CAPILLARY ELECTROPHORESIS

[76] Inventors: Hermanus H. Lauer, 2707 Ponce Ave., Belmont, Calif. 94002; Douglass McManigill, 250 Wilton Ave., Palo Alto, Calif. 94306

[*] Notice: The portion of the term of this patent subsequent to Jul. 5, 2011 has been disclaimed.

[21] Appl. No.: 213,879

[22] Filed: Mar. 15, 1994

Related U.S. Application Data

[63] Continuation of Ser. No. 346,428, May 1, 1989, Pat. No. 5,326,445.

[51] Int. Cl.$^6$ .................. G01N 27/26; G01N 27/447
[52] U.S. Cl. ................. 204/180.1; 204/299 R
[58] Field of Search ............... 204/180.1, 299 R

[56] References Cited

U.S. PATENT DOCUMENTS 5,207,886  5/1993  Lauer et al. ............... 204/180.1 X
5,326,445  7/1994  Lauer et al. ............... 204/180.1

Primary Examiner—John Niebling
Assistant Examiner—John S. Starsiak, Jr.

[57] ABSTRACT

In accordance with the present invention, a compliant pressure differential is applied across a separation column while its inlet is in a sample solution so that sample solution is introduced into the column. The profile of pressure differential over time is selected so that a desired volume of sample solution is introduced. Pressure and time are controlled with sufficient precision to yield repeatability of 5%, and preferably within 1%, by volume. The pressure differential is sufficiently low and the time sufficiently long that an acceptable velocity profile can be achieved.

1 Claim, 3 Drawing Sheets

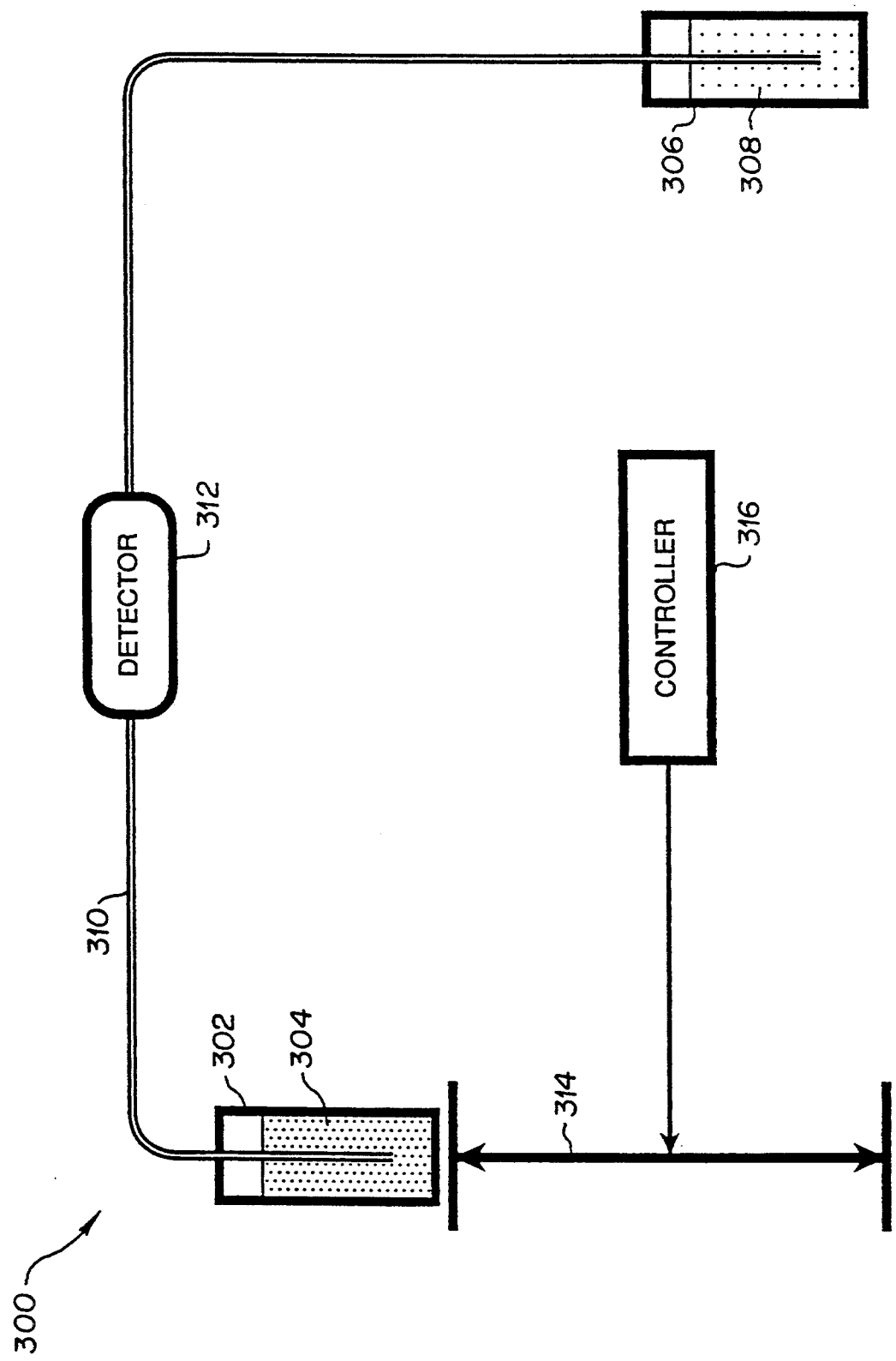

VACUUM INJECTION CAPILLARY ELECTROPHORESIS

CROSS REFERENCE TO RELATED APPLICATION

This is a continuation of application Ser. No. 07/346,428 now U.S. Pat. No. 5,326,445 filed on 1 May 1989.

BACKGROUND OF THE INVENTION

The present invention relates to chemical analysis and, more particularly, to an improved method for capillary electrophoresis. A major objective of the present invention is to provide for more convenient and precise determinations of the absolute concentration of a sample component in a sample solution.

Chemical analyses of complex organic structures has made noteworthy advances in biotechnology possible. Biotechnology has provided techniques for manufacturing life-supporting medicines and other products which would otherwise be in short supply if natural sources had to be relied upon. In addition, entirely new medical products are in development which may arrest and cure heretofore untreatable diseases. Biotechnology promises new products for agriculture which will feed the world's expanding populations and which will enhance the ability of famine-prone countries to sustain themselves.

Chemical analysis of biological samples generally involves the separation of the samples into components for identification and quantification. Capillary zone electrophoresis (CZE) is one of a class of methods in which the different components are moved within a narrowbore capillary at respective and different rates so that the components are divided into distinct zones. The distinct zones can be investigated within the capillary or outside the capillary by allowing the components to emerge from the capillary for sequential detection.

In CZE, a sample is introduced at an input end of a longitudinally extending capillary and moved toward an output end. Electrodes of different potentials at either end of the capillary generate the electrical forces which move the sample components toward the output end of the capillary. This movement includes two distinct components, one due to electro-osmotic flow and the other due to electrophoretic migration.

One of the applications of CZE is to determine the absolute concentration of a sample component in a sample solution. The quantity of a sample component eluting from a separation column can be determined by integrating its detection peak to determine the area represented by the component.

However, the quantity of sample solution from which the component quantity was separated is not easily ascertained. The problems of obtaining precise sample volume introductions have been studied in "Theory, Instrumentation, and Applications of Capillary Zone Electrophoresis" by Krynn DeArman Lukacs, a dissertation submitted in 1983 to the University of Carolina at Chapel Hill. This dissertation examined electrostatic introduction, using the same mechanism used by CZE for sample separation and concluded that precise volume control was not obtainable due to differential electrophoretic mobility of sample components. Various hydrostatic introductions were made, basically using syringes, but convective disturbances and parabolic flow profiles adversely affected the sample distribution in the column. The sample should be in the form of a compact cylindrical plug at the column head. Other shapes and distributions result in broader eluting bands and, thus, poorer detection sensitivity.

Attempts to determine sample quantities from the detected peaks have had limited success. It is not feasible to determine a total sample quantity by integrating over all eluting peaks. It is possible to introduce a known quantity of a identifiable component into a sample solution and use the area of its peak to determine the volume separated. However, the introduction of the identifiable component into the sample solution must be carefully controlled if useful results are to be obtained. More problematic is the selection of the identifiable component which must have a peak which will not interfere with the sample component peaks. It is often necessary to run a sample to find detection regions without peaks to select the sample. This is undesirably cumbersome.

What is needed is a convenient and reliable method for determine absolute concentrations of sample components.

SUMMARY OF THE INVENTION

In accordance with the present invention, a compliant pressure differential is applied across a separation column while its inlet is in a sample solution so that sample solution is introduced into the column. The profile of pressure differential over time is selected so that a desired volume of sample solution is introduced. Pressure and time are controlled with sufficient precision to yield repeatability of 5%, and preferably within 1%, by volume. The pressure differential is sufficiently low and the time sufficiently long that an acceptable velocity profile can be achieved. These and other features and advantages of the present invention are apparent from the description below with reference to the following drawings.

BRIEF DESCRIPTION OF THE DRAWINGS

FIG. 3 is a schematic diagram of another alternative sample injection system in accordance with the present invention.

DESCRIPTION OF THE PREFERRED EMBODIMENTS

Figure 1:
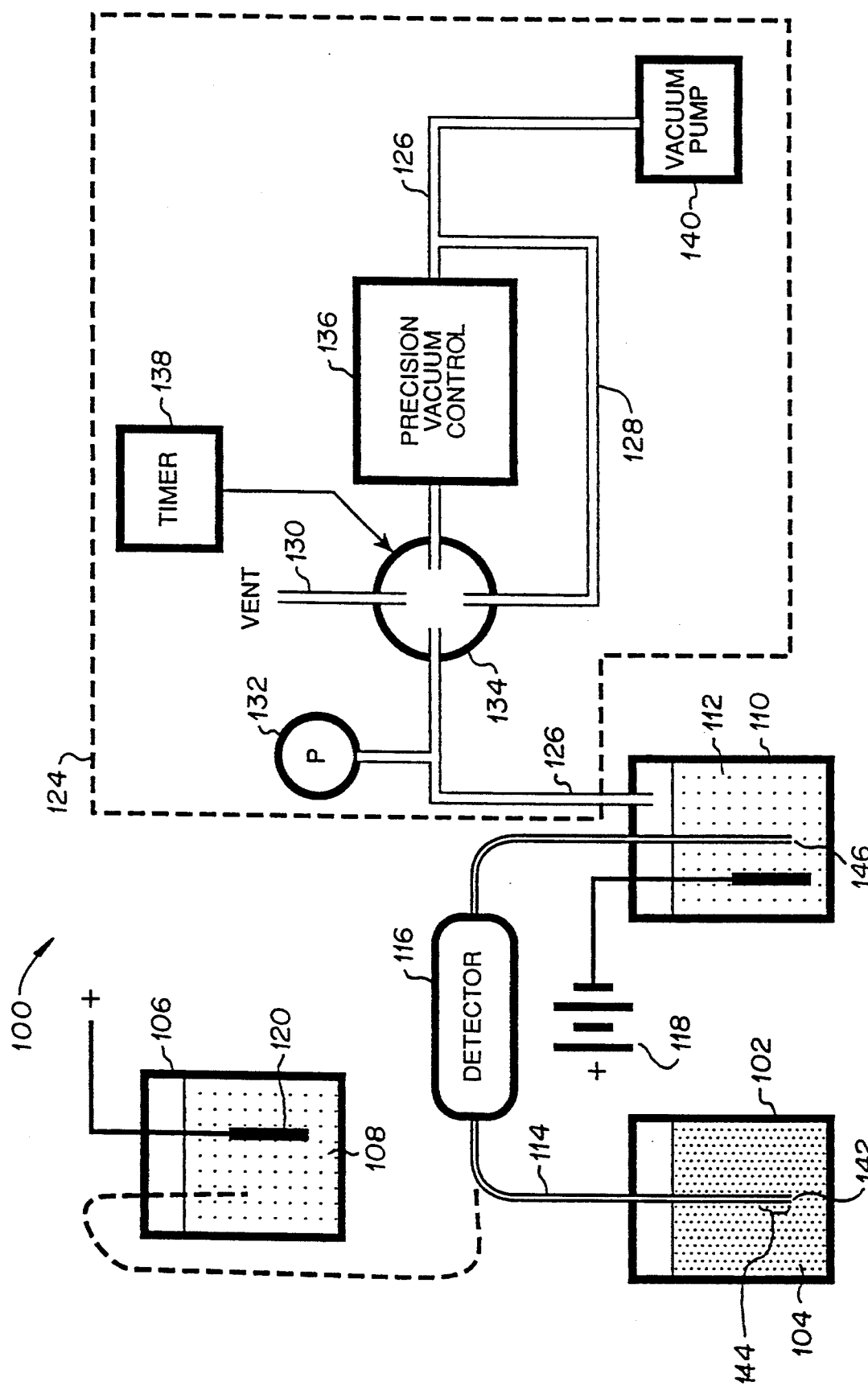
FIG. 1 is a schematic diagram of a capillary zone electrophoresis system in accordance with the present invention.

In accordance with the present invention, a capillary zone electrophoresis (CZE) system 100 comprises a sample reservoir 102 containing sample solution 104, an electrolyte reservoir 106 containing a carrier electrolyte 108, an effluent reservoir 110 containing an effluent electrolyte 112, a capillary separation column 114, a detector 116, a power supply 118, a positive electrode 120 within electrolyte reservoir 106, a negative electrode 122 within effluent reservoir 110, and a vacuum section 124. as shown in FIG. 1. Vacuum section 124 includes a main conduit 126, a bypass conduit 128, a vent conduit 130, a manometer 132, a 3-way valve 134, a precision vacuum controller 136, a timer 138, and a vacuum pump 140. Capillary column 114 includes an inlet end 142 at a column head 144 and an outlet end 146, disposed within effluent electrolyte 112.

System 100 differs from convention CZE systems in its provision for vacuum introduction of sample solution 104 into the separation column 114. Prior to sample introduction, inlet end 142 is inserted into electrolyte reservoir 106 so that carrier electrolyte 108 can be used to flush and fill separation column 114. This filling and flushing is facilitated by a relatively strong vacuum effected by vacuum pump 140 while valve 134 couples bypass conduit 128 to effluent reservoir 110.

Inlet end 142 is then inserted into sample reservoir 102, which is open to ambient pressure at its top. Precision vacuum control 136 establishes a predetermined relatively weak vacuum which is hyrdodynamically coupled to outlet end 146 via main conduit 126 and sealed effluent reservoir 110 by switching valve 134. Timer 138 is initiated as valve 134 is switched to couple precision vacuum controller 136 and then causes controller 136 to switch to vent conduit 130 after a predetermined time has elapsed.

Coupling vent conduit 130 to effluent reservoir 110 removes the pressure differential across column 114. With the pressure different removed, inlet end 142 is inserted into electrolyte reservoir 106 and power supply 118 is switched on so that carrier electrolyte 108 flows from electrolyte reservoir 108 through column 114 to effluent reservoir 110, effecting sample separation as known in the CZE art. Detector 116 detects the eluting peaks as they serially progress through column 114.

The pressures and times used for sample injection are selected to ensure that the correct volume of sample solution is introduced into column head 144. Depending on column diameters, which can range from 10 $\mu$m to 100 $\mu$m, pressure differentials from about 1 centimeter of water to near 15 meters of water can be used for sample injection, with injection times being from about 1 second to about 50 seconds. Longer introduction times provide for flatter velocity profiles over a diameter of head 144, with diminishing returns setting at the longest times. Thus, introduction times of 3–20 seconds are preferred.

Precise volume control is critical to obtaining repeatability required to determine the absolute concentration of a sample in the sample solution. Average pressure differentials should be maintainable within 5%, and preferably, within 1%, of nominal levels. Such control is obtainable using a Veriflow BPR40 "Back Pressure Regulator" modified for vacuum use. Alternatively, a suitable precision vacuum regulator is available from Testcom.

The desired average pressure can be established by holding a constant pressure at the desired average level. In this case, it is important to minimize transition times at the start and finish of the sample introduction procedure. The transition to the desired pressure differential can be accelerated by including with precision pressure controller 136 a volume within which a desired pressure is established before connection is made to effluent reservoir 110. The volume serves as a buffer to that the loss of vacuum as connection is made to effluent reservoir 110 is negligible. A quick return to ambient pressure at the end of sample introduction is effectively handled by the switch to vent conduit 130.

Figure 2:
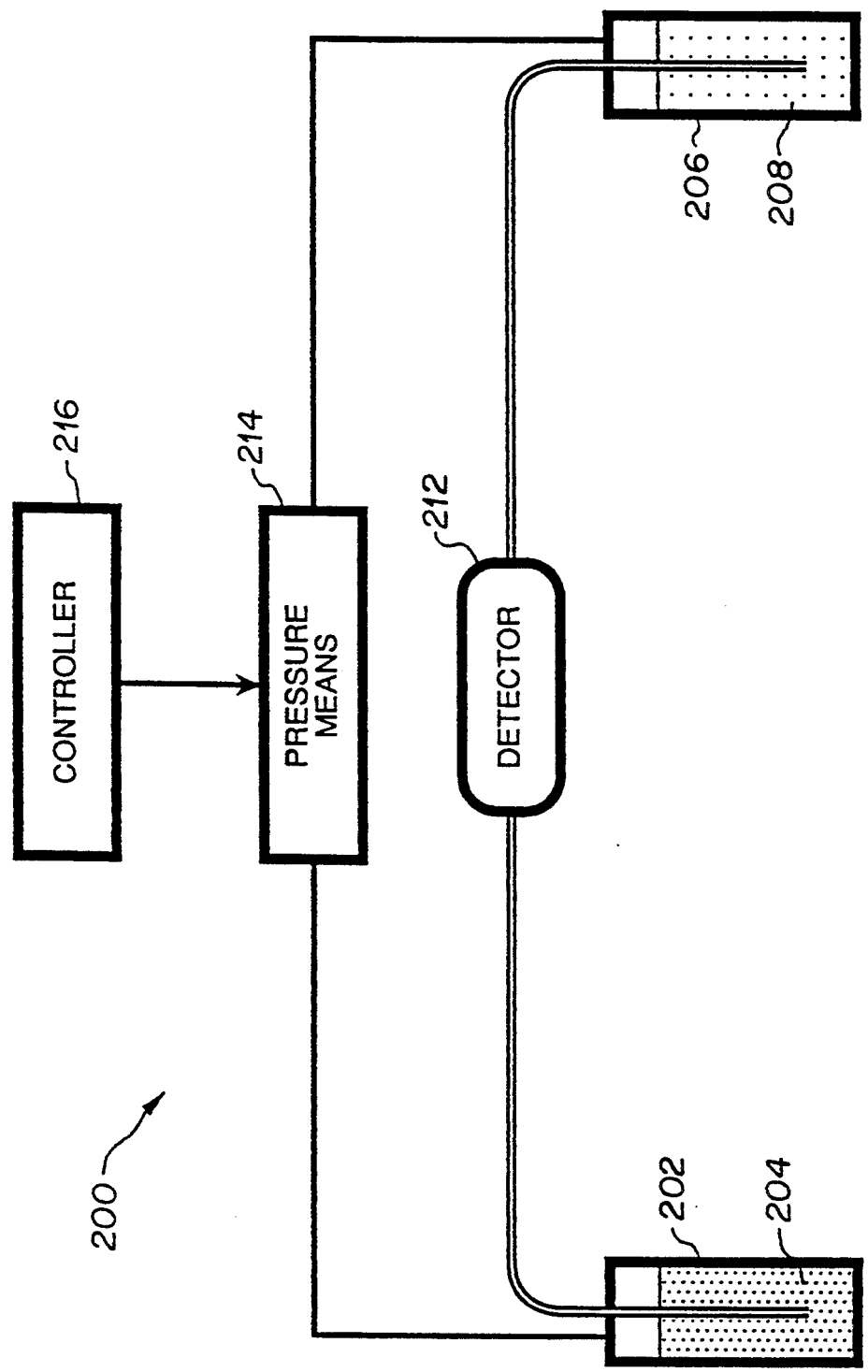
FIG. 2 is a schematic diagram of an alternative sample injection system in accordance with the present invention.

An alternative separation system 200 includes a sample reservoir 202 holding a sample solution 204, an effluent reservoir 206 holding an effluent electrolyte 208, a separation column 210 with a detector 212, pressure means 214 and a controller 216, as shown in FIG. 2. Pressure means 214 is connected to both reservoirs 202 and 206 to establish a pressure differential therebetween. This pressure differential can be established by pressurizing sample reservoir 202, applying a vacuum to effluent reservoir 206, or otherwise establishing the required pressure differential. Controller 216 regulates pressure means 214 to obtain the pressure profile over time required to introduce the desired sample volume while minimizing the velocity profile over the column diameter.

The concern for transition times are avoided by taking the entire pressure profile over time into account. In this case, it is not necessary to insure fast transitions or constant pressures between transitions. The profile can be selected so that the desired integral of pressure over time has the value required for the desired volume introduction. In fact, some turbulence can be avoided by using gradual pressure transitions.

Another separation system 300 includes a sample reservoir 302 holding a sample solution 304, an effluent reservoir 306 holding an effluent electrolyte 308, a separation column 310 with a detector 312, elevation means 314 and a controller 316, as shown in FIG. 3. In this case, the desired hydrodynamic introduction of sample solution 304 into column 314 is effected by elevating sample reservoir 302 relative to effluent reservoir 306. Controller 316 regulates the height differential by controlling elevation means 314, returning sample reservoir 302 to the level of effluent reservoir 306 once the desired sample volume is introduced.

The present invention provides for highly repeatable separation techniques so that absolute component concentrations can be determined. Many variations upon and modification to the disclosed embodiments are provided for by the present invention, the scope of which is limited only by the following claims.

What is claimed is:

1. A method for injecting a predetermined volume of sample into a separation column, the method comprising the steps of:

inserting an inlet end of a capillary column into a sample solution;

setting a timer to a time interval calculated to inject the predetermined volume, the time interval being between 1 second and 50 seconds; and applying a constant pressure differential between the inlet end and an outlet end of the column such that the outlet end is at a lower pressure than the inlet end, wherein the constant pressure differential is maintained within 5% of a predetermined pressure differential between about 1 centimeter of water and 10 meters of water.

* * * * *